(12) United States Patent
Mentkow et al.

(10) Patent No.: US 9,474,652 B2
(45) Date of Patent: Oct. 25, 2016

(54) HEMOSTATIC AGENT DELIVERY SYSTEM

(76) Inventors: Jack Mentkow, Wellington, FL (US);
Lisa Mentkow, Wellington, FL (US)

(*) Notice: Subject to any disclaimer, the term of this patent is extended or adjusted under 35 U.S.C. 154(b) by 1900 days.

(21) Appl. No.: 11/453,524

(22) Filed: Jun. 15, 2006

(65) Prior Publication Data

US 2007/0160638 A1 Jul. 12, 2007

Related U.S. Application Data

(60) Provisional application No. 60/757,459, filed on Jan. 9, 2006.

(51) Int. Cl.
*A61B 17/08* (2006.01)
*A61F 13/00* (2006.01)
(Continued)

(52) U.S. Cl.
CPC ... *A61F 13/00034* (2013.01); *A61F 13/00059* (2013.01); *A61F 13/00063* (2013.01); *A61L 15/18* (2013.01); *A61L 15/24* (2013.01); *A61L 15/28* (2013.01); *A61L 15/44* (2013.01); *A61F 2013/0054* (2013.01); *A61F 2013/00153* (2013.01); *A61F 2013/00472* (2013.01); *A61F 2013/00536* (2013.01);
(Continued)

(58) Field of Classification Search
CPC .................. A61F 13/00034; A61F 13/00063; A61L 15/18; A61L 15/60
USPC ................ 604/41–79; 602/48; 424/683–684; 606/201
See application file for complete search history.

(56) References Cited

U.S. PATENT DOCUMENTS 3,349,909 A * 10/1967 Studer .......................... 209/207
4,822,349 A 4/1989 Hursey et al.
(Continued)

FOREIGN PATENT DOCUMENTS

WO WO 9959647 A1 * 11/1999 ............. A61L 15/32
WO 2006088912 A2 8/2006
(Continued)

OTHER PUBLICATIONS

Hemcon: The Remarkable Hemcon Bandage is Designed to Control Severe Bleeding and Save Lives. http://www.hemcon.com/home.html (© 2004 Hemcon, Inc.).
(Continued)

*Primary Examiner* — Gregory Anderson
*Assistant Examiner* — Christina Lauer
(74) *Attorney, Agent, or Firm* — Laurence A. Greenberg; Werner H. Stemer; Ralph E. Locher

(57) ABSTRACT

A hemostatic agent delivery system includes a hemostatic agent which is inert and non-reactive yet is capable of forming a stable clot when applied to an actively bleeding wound. The system also includes a delivery assembly to structure to facilitate delivery of the hemostatic agent proximate the hemorrhage site. More specifically, the delivery assembly is structured to releasably contain the hemostatic agent via a release member which is disposed in cooperative relation with a support member which contains the amount of the hemostatic agent. The release member is structured of a soluble material such that it will at least partially dissolve and release the hemostatic agent upon disposition proximate the hemorrhage site. The delivery assembly further comprises a handle member structured to facilitate delivery of the hemostatic agent to the hemorrhage site.

42 Claims, 3 Drawing Sheets

(51) Int. Cl.
  *A61L 15/18* (2006.01)
  *A61L 15/24* (2006.01)
  *A61L 15/28* (2006.01)
  *A61L 15/44* (2006.01)

(52) U.S. Cl.
  CPC .............. *A61F 2013/00642* (2013.01); *A61F 2013/00982* (2013.01); *A61L 2300/418* (2013.01); *A61L 2300/602* (2013.01); *A61L 2400/04* (2013.01)

(56) References Cited

U.S. PATENT DOCUMENTS

| | | | |
|---|---|---|---|
| 5,056,510 | A | 10/1991 | Gilman |
| 5,429,591 | A | 7/1995 | Yamamoto et al. |
| 5,478,308 | A | 12/1995 | Cartmell et al. |
| 5,800,372 | A | 9/1998 | Bell et al. |
| 5,891,078 | A * | 4/1999 | Turngren et al. ............... 602/58 |
| 5,899,871 | A | 5/1999 | Cartmell et al. |
| 5,944,933 | A | 8/1999 | Heller et al. |
| 6,007,837 | A * | 12/1999 | Enscore et al. ............... 424/449 |
| 6,060,461 | A | 5/2000 | Drake |
| 6,114,594 | A | 9/2000 | Barikosky |
| 6,521,265 | B1 | 2/2003 | Patterson |
| 6,568,398 | B2 | 5/2003 | Cohen |
| 6,897,348 | B2 | 5/2005 | Malik |
| 6,998,510 | B2 | 2/2006 | Buckman et al. |
| 7,455,680 | B1 * | 11/2008 | Ashby et al. ............... 606/213 |
| 2003/0040692 | A1 * | 2/2003 | Rothwell et al. ............... 602/48 |
| 2003/0109820 | A1 | 6/2003 | Gross et al. |
| 2003/0133990 | A1 * | 7/2003 | Hursey et al. ............... 424/601 |
| 2003/0176828 | A1 * | 9/2003 | Buckman et al. ............. 602/48 |
| 2004/0167479 | A1 * | 8/2004 | Warren et al. ............... 604/289 |
| 2004/0193088 | A1 * | 9/2004 | Looney et al. ............... 602/48 |
| 2005/0209567 | A1 * | 9/2005 | Sibbitt, Jr. ................... 604/187 |
| 2005/0266081 | A1 * | 12/2005 | Rogozinski ................... 424/484 |
| 2005/0277577 | A1 | 12/2005 | Hunter et al. |
| 2006/0002976 | A1 | 1/2006 | Kronenthal |
| 2006/0015235 | A1 | 1/2006 | Ringger et al. |
| 2006/0155235 | A1 * | 7/2006 | Sawyer ........................... 602/48 |
| 2007/0160638 | A1 | 7/2007 | Mentkow et al. |

FOREIGN PATENT DOCUMENTS

| | | | |
|---|---|---|---|
| WO | WO 2006088912 A2 * | 8/2006 | ............ A61L 26/00 |
| WO | 2007081760 A2 | 7/2007 | |

OTHER PUBLICATIONS

International Search Report and Written Opinion dated Feb. 24, 2009.

Lordan et al., "Cytotoxic effects induced by unmodified and organically modified nanoclays in the human hepatic HepG2 cell line", Research Article, Journal of Applied Toxicology, Published online in Wiley Online Library, Jul. 30, 2010.

Hasmukh et al., "Nanoclays for polymer nanocomposites, paints, inks, greases and cosmetics formulations, drug delivery vehicle and waste water treatment", Bull. Mater. Sci., vol. 29, No. 2, Apr. 2006, pp. 133-145, Indian Academy of Sciences.

Nanotechnology Development Blog, Nanotechnology development news and information, "New Nanoclay developed by Iranian University", Dec. 4, 2008.

Elementis Specialties, "Additives for Construction Systems—Tile Adhesives—Rendering/Plasters/Stuccos—EIFS Gypsum Flooring—Bituminous and Asphalt Systems", Printed in Belgium—Jan. 2004, www.elementis-specialties.com.

Patel, Hasmukh, et al. "Nanoclays for polymer nanocomposites, paints, inks, greases and cosmetics formulations, drug delivery vehicle and waste water treatment", Bulletin, Material Science, vol. 29, No. 2, Apr. 2006, pp. 133-145, Indian Academy of Sciences.

* cited by examiner

HEMOSTATIC AGENT DELIVERY SYSTEM

CLAIM OF PRIORITY

The present application is based on and a claim to priority is made under 35 U.S.C. Section 119(e) to provisional patent application currently in the U.S. Patent and Trademark Office having Ser. No. 60/757,459 and a filing date of Jan. 9, 2006.

BACKGROUND OF THE INVENTION

1. Field of the Invention

The present invention is directed to a hemostatic agent delivery system comprising a delivery assembly having a pouch or receptacle containing a hemostatic agent, the pouch being at least partially defined by a support number in combination with an overlying release member made of a soluble material. More in particular, the hemostatic agent delivery system is structured such that a hemostatic agent is delivered directly to a source of bleeding, and wherein the hemostatic agent is concentrated and retained at the bleeding source to facilitate clotting and terminate hemorrhaging.

2. Description of the Related Art

It has long been known that injuries which result in excessive bleeding if not quickly or properly addressed can often prove fatal. Unfortunately, this fact is well supported by data gathered during numerous armed conflicts throughout time. For instance, it has been reported that over 2,500 soldiers died from extremity wounds during the Vietnam War solely because they bled to death. Military data also indicate that approximately 50% of combat casualties die from bleeding, and that the majority die within thirty minutes of the injury. It has also been reported that of the fifty %, approximately sixty % die within the first five minutes while the remaining persons die within one hour if not properly treated.

In addition, it has been estimated that there are over seventy million emergency room visits each year for bleeding. As above, with respect to injuries sustained during battle, bleeding or acute hemorrhaging is a leading cause of death in trauma cases among the civilian population.

As such, it is clear that rapid and effective control of hemorrhaging saves lives. Attempts to address the need for such rapid and effective hemorrhage control have resulted in a development of a number of so called hemostatic bandages and other products purported to facilitate rapid control of bleeding.

One such product comprises a granular zeolite material which may be obtained from volcanic lava rocks. This material is placed into a bleeding wound where it absorbs water molecules from the blood, thereby creating a high platelet concentration which promotes clotting. However, it has been observed that the absorption process affected by this zeolite is a highly exothermic reaction which generates a considerable amount of heat. This is believed to at least partially attributable to reaction with the iron content of the zeolite. More specifically, temperatures ranging from 90° to 100° C. have been reported following use of the material, causing second degree burns to soldiers injured and treated with this product in Iraq, as well as to those persons administering the product, even though personnel administering this product must be trained and certified to administer the same.

A further drawback to this product is that the zeolite material is packaged to be simply poured on to an open wound, however, in the case of hemorrhaging of any significance, such as may occur due to laceration of a major artery, the pressure of blood exiting the wound will simply cause the material to be dispersed thereby minimizing and/or eliminating the effectiveness of the clotting properties therein. Yet another disadvantage of this product is that the zeolite material is granular in nature, making it difficult to subsequently remove the material from the wound via normal means such as irrigation and/or suctioning of the wound area, once the injured person is transferred to an operating room or other such treatment facility.

Another product is made from chitosan, which is derived from the exoskeletons of shellfish. Reports as to the effectiveness of this device in hemorrhage control are conflicting, in particular, its effectiveness in the event of hypothermia in the patient, such as may occur from shock following significant blood loss, is reported to be severely reduced or diminished. In addition, there have been reports of the device being improperly applied, e.g., the wound is not contacted by the active surface due to the device being placed into the wound site upside down. Since this product is derived from living organisms, it has an extremely limited shelf life during which time it must either be utilized or disposed of, and given the significant cost of each unit, this is a further considerable disadvantage.

Another type of hemostatic bandage is manufactured from single cell algae and comprises poly-N-acetylglucosamine. This device is structured to enable persons with minimal training to quickly and effectively control and/or stop hemorrhaging from extremity trauma. More in particular, when the material comes in contact with blood it reportedly stimulates platelet aggregation and activation which causes the body to secrete tromboxane, which stimulates the blood vessels to constrict in the vicinity of the wound. Stated differently, the poly-N-acetylglucosamine material acts as a catalyst to accelerate the normal clotting process thereby accelerating the bodies own control of the bleeding. Once again, since this product is derived from living organisms, it has a limited shelf life during which it must be utilized or disposed. Further, its effectiveness in the event of hypothermia in the patient, such as in the above example, is questionable.

Another material which is structured to be applied, i.e., poured, directly to wounds has been synthesized from potato starch. Reportedly, the particles accelerate natural clotting by concentrating blood solids forming a gel around the same so as to promote clotting. In particular, the larger particles of the blood components are concentrated on the surface of the synthesized potato starch product, thereby promoting accelerate clotting. As noted, this material is also in a powder form and has been applied directly to a bleeding wound with a bellows type applicator as noted above with respect to the zeolite material, however, in the event of excessive bleeding such as a major artery, the pressure of the blood flowing from the wound is often sufficient to disperse the powder thereby once again, minimizing or eliminating the clotting property exhibited therein, even though the wound site is to be covered with a standard bandage and pressure applied after treatment with the synthesized potato starch material.

Yet another powdered material is composed from a hydrophilic polymer and a potassium salt in combination with a bovine based thrombin material. This powder is also reported to stop bleeding on contact based upon studies for various minor wounds, in which no covering bandage is required, however, as noted above with respect to the other "pour" type products, in the event of any significant bleeding, the blood pressure itself its likely to disperse the product, thereby reducing or eliminating any hemostatic it was intended to affect.

In view of the foregoing, it is clear that it would be a significant benefit to provide a system for rapid, effective, and efficient control of hemorrhaging including hemorrhaging of major arteries, which may be quickly and properly applied by personnel with minimal training. More in particular, it would be beneficial to provide a system for delivering an effective amount of a hemostatic agent directly to a wound site, as well as providing a mechanism to maintain an effective amount of the hemostatic agent at the wound site to control bleeding. Also, it would be advantageous for such a system to comprise a hemostatic agent which is essentially nonreactive and hypoallergenic when applied to a wound. Further, the hemostatic agent employed in such a system should promote clotting of the blood in a non-reactive manner, i.e., without exothermic reaction with the blood and the localized temperature increase associated therewith. Yet another advantage may be realized by providing such a system with a hemostatic agent which is inorganic, thereby benefiting from an essentially indefinite shelf life.

SUMMARY OF THE INVENTION

The present invention is directed to a hemostatic agent delivery system which is structured to deliver a hemostatic agent directly to a hemorrhage site, for example, a lacerated artery, so as to facilitate clotting of the blood and terminate hemorrhaging at the site. As such, the hemostatic agent delivery system of the present invention is further structured to concentrate and retain the hemostatic agent at the hemorrhage site, once again, to facilitate clotting and terminate hemorrhaging.

At least one embodiment of the delivery system of the present invention includes at least one hemostatic agent structured to facilitate blood clotting. More in particular, at least one hemostatic agent of the present invention comprises a smectite clay material. In at least one further embodiment, a hectorite clay is utilized as the hemostatic agent. The present invention encompasses the utilization of a clay material as a hemostatic agent either alone or in combination with one or more additive, as is discussed further below.

To facilitate delivery of the hemostatic agent to a hemorrhage site, the delivery system of the present invention further comprises a delivery assembly which is structured to at least temporarily contain an amount of the hemostatic agent, at least until the agent is delivered proximate to a hemorrhage site. The delivery assembly, in at least one embodiment, includes a release member disposed in overlying relation to a support member. More in particular, the release member and the support member are cooperatively structured to at least temperately contain the hemostatic agent therebetween, the release member and the support member being attached about their respective peripheries.

In order to achieve releasable containment of one or more hemostatic agent via the delivery assembly of the present invention, the release member comprises a soluble material structured to at least partially dissolve and release the hemostatic agent upon disposition directly proximate to a hemorrhage site. In at least one embodiment, the release member comprises a soluble polymeric material, such as, by way of example only, a polyvinyl alcohol material.

To further facilitate delivery of an amount of a hemostatic agent directly to a hemorrhage site, the delivery assembly of the present invention also includes a handle member attached to an outer surface of the support member, wherein the handle member is structured to facilitate handling of the delivery system by a user. At least one embodiment of the present invention includes a handle member having a visual indication to facilitate location or identification of the handle member by a user. This feature may prove critical in the hectic and often chaotic environment in which the hemostatic delivery system of the present invention is utilized, such as, and the battle field, field medical unit, or hospital emergency room.

The present invention further encompasses a method of application of a hemostatic agent to a hemorrhage site including the step of delivery an amount of a hemostatic agent, wherein the hemostatic agent comprises a beneficiated hectorite clay material, directly proximate the hemorrhage site. The method further includes concentrating the amount of hemostatic agent in a substantially conforming relation to the configuration of the hemorrhage site, and retaining the amount of the hemostatic agent at the hemorrhage site in a substantially occluding relation so to facilitate clotting and terminate hemorrhaging at the site. The method further provides for removing the hemostatic agent from the hemorrhage site via standard irrigation and suction procedures, once a patient has been stabilized and transferred, for example, to a fixed facility operating room or field operating unit. As noted above, the hemostatic agent of the present invention is structured to form a stable clot such that the patient may be moved, once hemorrhaging has been terminated.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
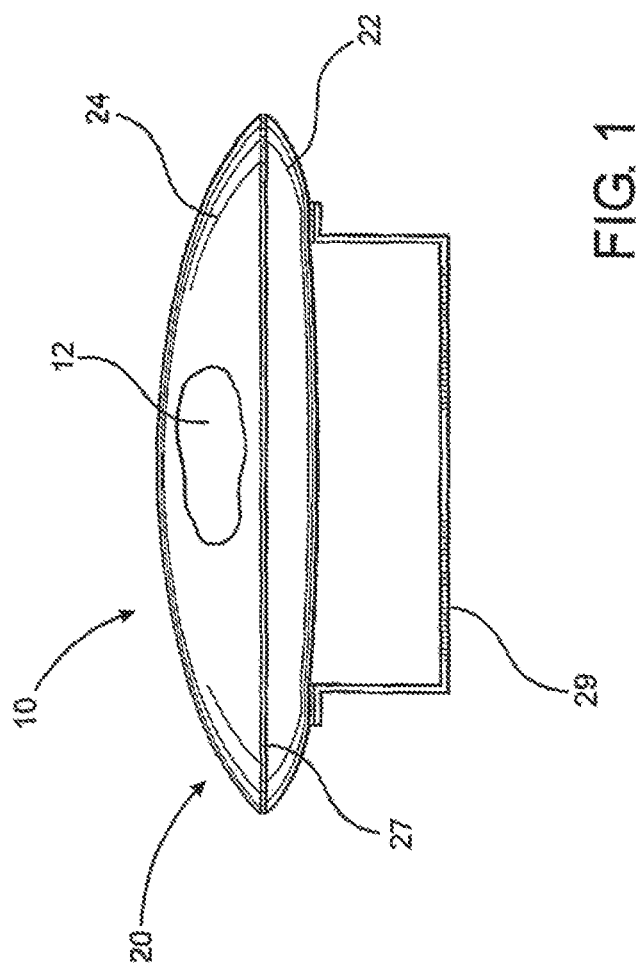
FIG. 1 is a perspective view of one preferred embodiment of a hemostatic agent delivery system in accordance with the present invention.

As previously noted, the present invention is directed to a hemostatic agent delivery system, generally as shown as 10 in the figures, which is structured to facilitate delivery of a hemostatic agent directly proximate a hemorrhage site. More in particular, the present invention is directed towards a hemostatic agent delivery system 10 which may be quickly and effectively utilized to facilitate clotting and to control and/or terminate hemorrhaging of an injured person, such as, a soldier wounded on a battle field, by personnel with minimal training. As will become apparent from the following, the hemostatic agent delivery system 10 of the present invention is structured such that personnel with minimal instruction in its use will be able to readily identify the proper orientation of the delivery assembly 20, so as to facilitate disposition of the delivery assembly 20 directly proximate a hemorrhage site.

To reduce and/or terminate excessive bleeding at a hemorrhage site, the hemostatic agent delivery system 10 of the present invention comprises at least one hemostatic agent 12. Of course, is within the scope and intent of the present invention to comprise a plurality of hemostatic agents 12, or a combination of one or more hemostatic agent 12 and one or more additives, such as may be desirable to enhance the performance of one or more hemostatic agent 12. As one example, the hemostatic agent 12 of the present invention, in at least one embodiment, comprises a hydroxyethyl cellulous additive structured to enhance the absorption of water from the blood by the hemostatic agent 12, thereby increasing the rate of clot formation, and termination of the hemorrhage. As noted above, bleeding is a major cause of death in both military and civilian injuries, and the present invention enables quick and effective control and/or termination of hemorrhaging, which is proven to save lives.

In at least one embodiment of the present invention, at least one hemostatic agent 12 comprises smectite clay. Smectite is a family of naturally occurring layered swelling clays which include bentonite, also known as montmorillonite, hectorite, and saponite. More in particular, the smectite clays are layered silicates which swell in water, and are widely used as rheological additives. Specifically, the silicate platelets comprise three layers, two silicate dioxide layers which embed a metal oxide layer. In bentonite clays, the metal oxide layer is mainly aluminum, whereas in hectorite clay the metal oxide layer comprises magnesium. More importantly, bentonite may include approximately 4% by weight of ferric and ferrous oxides, hectorite clay is essentially iron free, comprising generally less than one-half of one percent (<0.50%) by weight. This is important, as a presence of iron is believed to promote exothermic reactions between hemostatic agents and body fluids during absorption processes. A further benefit of hectorite clay, for use in conjunction with the present invention, is that it can be highly beneficiated, i.e., purified and ground, such that the particle size of hectorite clay is approximately 10% that of similar bentonite clays. One preferred embodiment of the present invention comprises a beneficiated hectorite clay as a hemostatic agent 12. More in particular, the present invention may comprise Bentone EW® which is a highly beneficiated hectorite clay available from Elementis Specialties of Hightstown N.J. Bentone EW® has a density of about 2.5 grams per cubic centimeters (g/cm$^3$) and, more importantly, a particle size distribution wherein approximately 94% or greater of the material is less than 200 mesh screen size.

Of course, as noted above, the present invention comprises a hemostatic agent delivery system 10 comprising a plurality of hemostatic agents 12, as one example, at least one embodiment may comprise bentonite clay, or a combination of hectorite and bentonite clays in a variety of proportions. Also as noted above, one or more additives may be combined with the hemostatic agent 12 to enhance the hemostatic properties thereof. As just one example, in one further preferred embodiment of the present invention the hemostatic agent 12 comprises a highly beneficiated hectorite clay in combination with a hydroxyethyl cellulous additives. More in particular, the hemostatic agent 12 of one preferred embodiment comprises Bentone LT® once again, available from Elementis Specialties.

An important consideration for selection of the hemostatic agent 12 for use in the present invention is that the agent 12 be essentially inert and non-reactive when disposed in contact with in open wound, and the blood or other body fluids being released therefrom. More in particular, as noted above, the hectorite clays do not include iron components to any significant degree therefore they are essentially non exothermic upon contact with water, blood, or other aqueous or bodily fluids. In addition, because of the powdered physical configuration of beneficiated hectorite clay, it serves to aid in the formation of a stable clot upon application to a hemorrhage site. Specifically, Bentone EW® is purified and pulverized into a fine power in the beneficiating process thereby increasing the effective surface area of the material, and resulting in an increase in absorptive capacity for removing the water content of blood so as to concentrate the blood platelets to facilitate clotting and to form a stable clot at the hemorrhage site. In tests conducted on swine, stable clots were formed at a hemorrhage site consisting of a lacerated femoral artery utilizing the hemostatic agent delivery system 10 and hemostatic agent 12 in accordance with the present invention.

The hemostatic delivery system 10 of the present invention further comprises a delivery assembly 20 which is structured to facilitate disposition of an amount of a hemostatic agent 12 directly proximate a hemorrhage site. More in particular, the delivery assembly is structured to releasably contain an amount of the hemostatic agent 12 for delivery to a hemorrhage site. In one preferred embodiment, the delivery assembly 20 includes a release member 24 which is disposed in overlying relation to an oppositely disposed support member 22, the release member being attached to and about a periphery of the support member 22. More in particular, the release member 24 and the support member 22 are cooperatively structured so as to at least temperately contain the amount of hemostatic agent 12 for delivery to a hemorrhage site, as illustrated in FIG. 1.

In at least one embodiment, the support member 22 comprises a sterile dressing, such as, by way of example, an anti-stick gauze pad. It will be appreciated, given the nature of the present invention, that each of the components comprising the delivery system 10 will be sterilized and packaged utilizing appropriate procedures to assure that a hemorrhage site is not exposed to external contamination. It will be further be appreciated, that a support member 22 comprising a sterile gauze pad will facilitate conforming the hemostatic agent delivery system 10 of the present invention substantially about the configuration of a wound so as to occlude the wound to facilitate the reduction and termination of hemorrhaging therefrom.

Looking next to the release member 24 of the present invention, the release member 24 comprises a soluble material of construction which is structure to at least partially dissolve upon contact with an aqueous solution, such as blood discharging from a wound. Upon dissolving, the release member 24 of the present invention will release the amount of hemostatic agent 12 from the delivery assembly 20 directly proximate to the hemorrhage site in a rapid and effective manner. In at least one embodiment, the delivery assembly 20 of the present invention comprises a release member 22 constructed of the soluble polymeric material which is structured to dissolve in blood and body fluids therewith.

In one preferred embodiment, the release member 22 comprises a polyvinyl alcohol material which will substantially dissolve upon contact with blood at a hemorrhage site. The polyvinyl alcohol material of the release member 22 may be constructed of any of a variety of thicknesses, thereby controlling the rate at which the release member 22 will dissolve and, as such, the rate at which the hemostatic agent 12 will be delivered to a hemorrhage site, a factor which is also affected by the volume of fluid present. As such, the hemostatic agent delivery system 10 of the present invention may be customized for application to a variety of wounds of varying degrees of severity. In at least one embodiment, the polyvinyl alcohol material comprises Super Solvy™, available from Sulky of America, Port Charlotte, Fla.

As one example, the hemostatic agent 12 may be applied directly proximate a superficial wound, in which case, the release member 22 will preferably comprise a very thin material so as to permit rapid dissolution and release of the hemostatic agent 12. For more severe hemorrhages, for example, laceration of a major artery, the release member 22 will comprise a greater thickness, to assure that the hemostatic agent delivery system 10 may be disposed proximate the hemorrhage site and configured to substantially conform to the wound prior to dissolution of the release member 24 and subsequent release of the hemostatic agent 12 to the hemorrhage site.

To facilitate attachment of the release member 24 to the support member 22, the delivery assembly 20 of the present invention further comprises a seal mechanism 27 structured to facilitate attachment between the members. More in particular, the seal mechanism 27 of the present invention comprises at least one seal member 28 which is structured to hermetically seal the release member 24 to the support member 22. In at least one embodiment of the present invention, the seal member 28 comprises a heat reactive adhesive. In one further embodiment, the seal member 28 comprises a HeatnBond® UltraHold iron-on adhesive, available from Therm O Web of Wheeling, Ill. Of significance is that the seal member 28 of this embodiment is structured to bond two dissimilar materials, each of which independently are structured to be non-adhesive, thereby forming a hermetically sealed pouch 21 which releasably contains one or more hemostatic agent 12.

Figure 2:
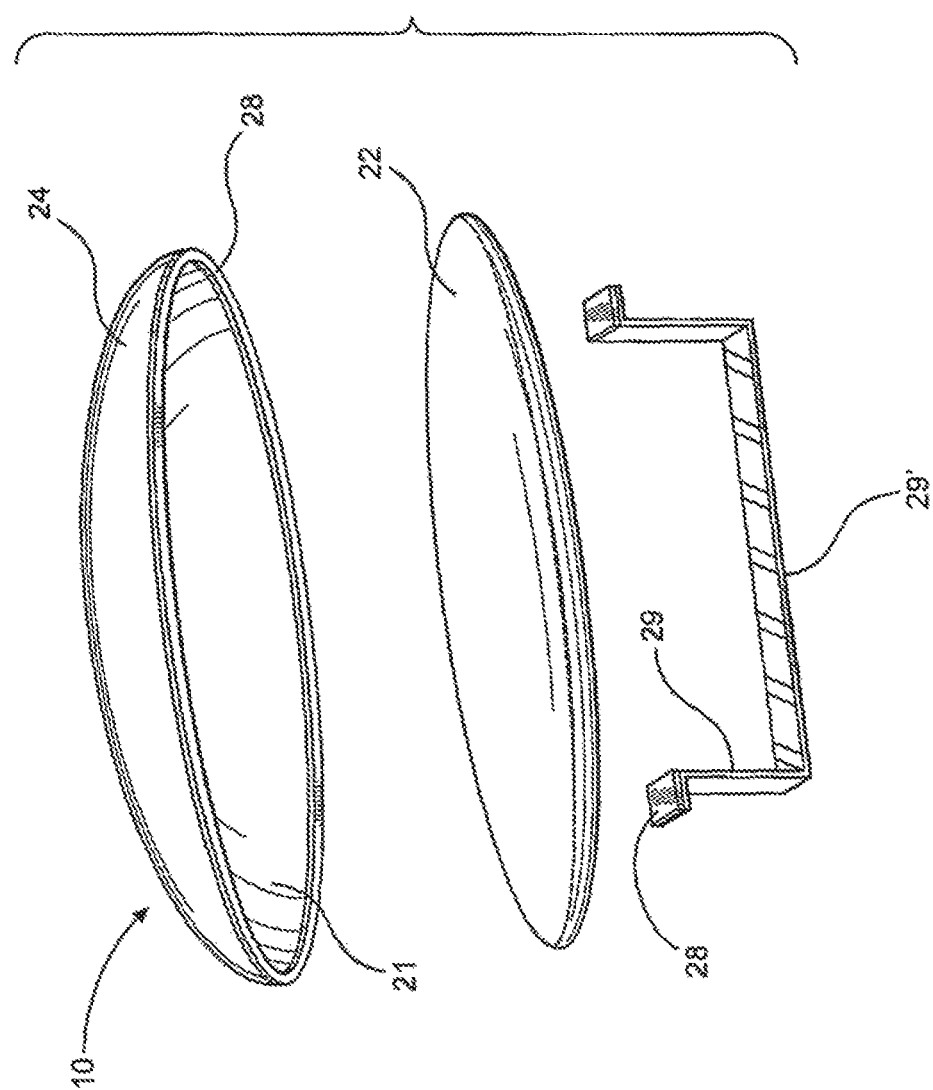
FIG. 2 is a partially exploded view of the embodiment of FIG. 1.

In at least one embodiment, the delivery assembly 20 of the present invention further comprises a handle member 29, as illustrated in the figures. The handle member 29, serves several purposes, the first of which being to facilitate disposition of the delivery assembly 20 directly proximate a hemorrhage site to facilitate delivery of a hemostatic agent thereto. More in particular, the handle member 29 is structured and configured to be grasped by one hand of a user and allow the user to quickly and effectively direct the surface of the delivery assembly 20 comprising the release member 24 directly onto a hemorrhage site, such as, a lacerated artery. As seen in FIGS. 1 and 2, the handle member 29 is attached to an outer face of support member 22 and disposed opposite the outer surface of the release member 24, and as such, the handle member 29 allows for the user to grasp the delivery assembly 20 with hands that may be wet or bloody, yet hindering contact with the release member 24, so as to prevent inadvertent and premature release of the hemostatic agent 12.

In at least one embodiment, the handle member comprises a visual indication 29, to facilitate location of the handle member 29 by a user. More in particular, the visual indication 29' may include indicia such as letters, symbols, stripes, etc., applied directly onto the handle member 29 as shown in FIG. 2. In at least one embodiment, the visual indication 29' may comprise a color contrast between the support member 22, typically being a white color sterile gauze pad, and the handle member 29, which may comprise a bright color or color pattern, for example, a striped pattern as illustrated in FIG. 2.

Figure 3:
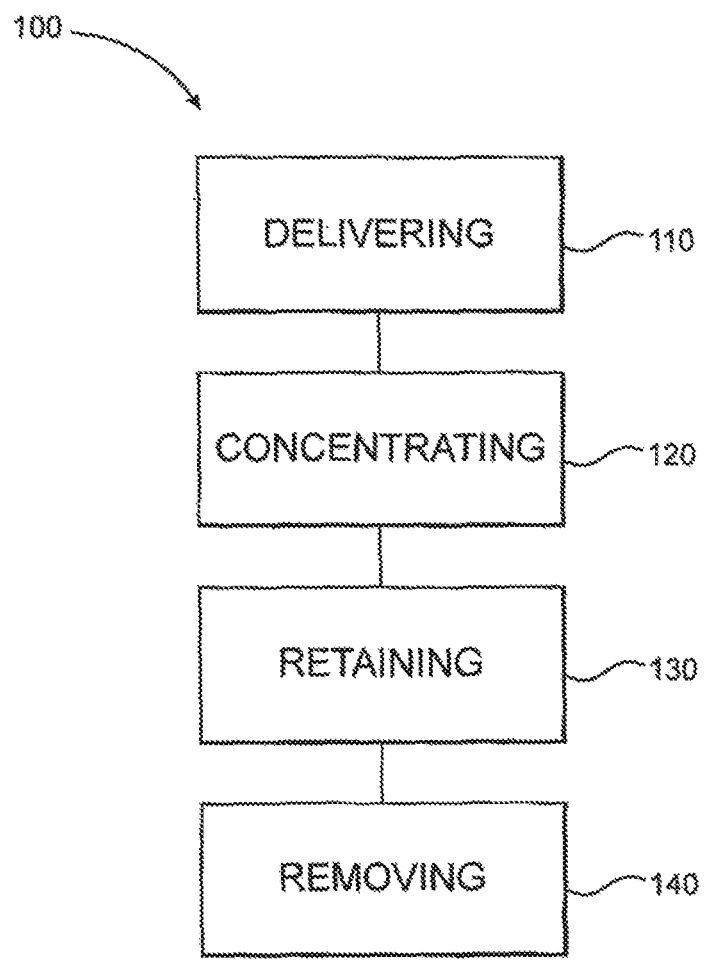
FIG. 3 is a diagramatic representation of a method of application of a hemostatic agent in accordance with the present invention.

As indicated above, the present invention further comprises a method for application of a hemostatic agent to a hemorrhage site, generally as illustrated at 100 in FIG. 3. More in particular, the method 100 of the present invention comprises delivering 110 an amount of a hemostatic agent comprising a beneficiated hectorite directly proximate a hemorrhage site. The method 100 further comprises concentrating 120 the amount of the hemostatic agent in a substantially conforming relation to the configuration of the hemorrhage site, and retaining 130 the amount of the hemostatic agent at the hemorrhage site in a substantially occluding relation to the hemorrhage site so as to facilitate clotting and terminate hemorrhaging therefrom. In at least one embodiment, the method 100 of the present invention further comprises the step of removing 140 the amount of the hemostatic agent from the hemorrhage site via irrigation and suction, once a patient is stabilized, for example in transferred to a field hospital or an emergency room.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A hemostatic agent delivery system comprising:
    at least one hemostatic agent structured to facilitate blood clotting and including a beneficiated hectorite clay that is inert and non-reactive with blood,
    a delivery assembly structured to permit disposition of an amount of said hemostatic agent directly proximate a hemorrhage site,
    said delivery assembly structured to releasably contain said amount of said hemostatic agent,
    said delivery assembly comprising a release member disposed in an overlying relation to a support member and attached about a periphery thereof,
    said release member and said support member cooperatively structured to at least temporarily contain said amount of said hemostatic agent therebetween, and
    said release member comprising a soluble material structured to dissolve and release said amount of said hemostatic agent upon disposition of said soluble release member directly proximate to the hemorrhage site.

2. The system as recited in claim 1 wherein said hemostatic agent further comprises at least one additive.

3. The system as recited in claim 1 wherein said hemostatic agent further comprises a hydroxyethyl cellulose additive.

4. The system as recited in claim 1 wherein said release member comprises a soluble polymeric material structured to dissolve in blood.

5. The system as recited in claim 4 wherein said release member comprises a polyvinyl alcohol material structured to dissolve in blood.

6. The system as recited in claim 4 further comprising a seal mechanism structured to attach said release member to said support member.

7. The system as recited in claim 6 wherein said seal mechanism comprises at least one seal member structured to hermetically seal said release member to said support member.

8. The system as recited in claim 7 wherein said at least one seal member adheres by heat.

9. The system as recited in claim 6 wherein said release member attached to said support member at least partially defines a pouch structured to contain said amount of said hemostatic agent.

10. The system as recited in claim 6 wherein said support member comprises a soluble polymeric material.

11. The system as recited in claim 1 wherein said hemostatic agent has a particle size distribution approximately 94% or greater of less than 200 mesh screen size.

12. The system as recited in claim 1 wherein said support member comprises an absorbent non-soluble material.

13. A hemostatic agent delivery system structured to deliver a hemostatic agent directly to a hemorrhage site and to concentrate and retain said hemostatic agent at the hemorrhage site to facilitate clotting and terminate hemorrhaging, said system comprising:
   a delivery assembly structured to facilitate delivery of an amount of said hemostatic agent directly proximate a hemorrhage site on a patient,
   said delivery assembly structured to releasably contain said amount of said hemostatic agent,
   said delivery assembly comprising a release member disposed in an overlying relation to an oppositely disposed support member and attached about a periphery thereof to at least partially define a pouch to contain said amount of said hemostatic agent,
   at least one seal member comprising a heat reactive adhesive structured to hermetically seal said release member to said support member,
   said release member comprising a soluble material structured to dissolve and release said amount of said hemostatic agent upon disposition of said soluble release member directly proximate the hemorrhage site,
   a handle member attached to an outer surface of said support member and structured to be grasped by a user to facilitate and direct delivery of said amount of said hemostatic agent directly proximate to the hemorrhage site, and
   said hemostatic agent structured to form a stable clot such that the patient may be safely moved and including a beneficiated hectorite clay that is inert and non-reactive with blood.

14. The system as recited in claim 13 wherein said handle member comprises a visual indication to facilitate location by a user.

15. The system as recited in claim 14 wherein said visual indication comprises a color contrast between said support member and said handle member.

16. The system as recited in claim 15 wherein said handle member comprises a striped pattern.

17. The system as recited in claim 13 wherein said support member comprises a sterile dressing.

18. The system as recited in claim 17 wherein said sterile dressing comprises an absorbent gauze material.

19. The system as recited in claim 13 wherein said handle member comprises a visual indication to facilitate location by a user.

20. The system as recited in claim 13 wherein said seal mechanism comprises at least one seal member adhering by heat.

21. The system as recited in claim 13 wherein said handle member is configured to be grasped by one hand of the user to allow the user to direct said release member directly onto the hemorrhage site.

22. The system as recited in claim 13 wherein said hemostatic agent further comprises at least one additive.

23. The system as recited in claim 13 wherein said hemostatic agent further comprises a hydroxyethyl cellulose additive.

24. A hemostatic agent delivery system comprising:
   a hemostatic agent comprising at least a beneficiated hectorite clay that is inert and non-reactive with blood structured to absorb water from blood to facilitate clotting,
   a delivery assembly structured to permit delivery of an amount of said hemostatic agent proximate a hemorrhage site,
   said delivery assembly structured to releasably contain said amount of said hemostatic agent,
   said delivery assembly comprising a release member disposed in an overlying relation to an oppositely disposed support member and attached about a periphery thereof,
   a seal mechanism disposed between an interface of said release member and said support member and structured to provide a hermetic seal therebetween and to at least temporarily contain said amount of said hemostatic agent therein,
   said release member comprising a soluble material structured to dissolve and release said amount of said hemostatic agent upon disposition of said soluble release member directly proximate to the hemorrhage site, and
   a handle member attached to an outer surface of said support member to be grasped by a user to facilitate and direct delivery of said amount of said hemostatic agent directly proximate to the hemorrhage site, wherein said handle member comprises a visual indication to facilitate identification by a user.

25. The system as recited in claim 24 wherein said hemostatic agent is hypoallergenic, non-reactive with blood and inert.

26. The system as recited in claim 24 wherein said hemostatic agent further comprises a hydroxyethyl cellulose additive.

27. The system as recited in claim 24 wherein said delivery assembly is structured to substantially conform to a configuration of the hemorrhage site.

28. The system as recited in claim 27 wherein said delivery assembly is further structured to substantially occlude the hemorrhage site to facilitate clotting.

29. The system as recited in claim 24 wherein said hemostatic agent has a particle size distribution approximately 94% or greater of less than 200 mesh screen size.

30. The system as recited in claim 24 wherein said support member comprises an absorbent non-soluble material.

31. The system as recited in claim 24 wherein said seal mechanism comprises at least one seal member adhering by heat.

32. The system as recited in claim 24 wherein said hemostatic agent further comprises at least one additive.

33. A hemostatic agent and delivery system, comprising:
   at least one hemostatic agent including a beneficiated hectorite that is inert and non-reactive with blood clay for facilitating blood clotting; and a delivery assembly for permitting disposition of an amount of said hemostatic agent proximate a hemorrhage site;

said delivery assembly including a soluble release member at least temporarily retaining said amount of said hemostatic agent for release upon disposition of said soluble release member proximate to the hemorrhage site.

34. The system according to claim 33, wherein said delivery assembly includes a support member to at least temporarily retain said amount of said hemostatic agent.

35. The system according to claim 33, wherein said delivery assembly permits disposition of said amount of said hemostatic agent proximate the hemorrhage site by one hand of a user.

36. The system as recited in claim 33 wherein said hemostatic agent has a particle size distribution approximately 94% or greater of less than 200 mesh screen size.

37. The system as recited in claim 33 wherein said hemostatic agent further comprises at least one additive.

38. The system as recited in claim 33 wherein said hemostatic agent further comprises a hydroxyethyl cellulose additive.

39. A system for delivering medicine, the system comprising:

a soluble release member to be disposed at a hemorrhage site for retaining the medicine and dissolving for releasing the medicine where desired, the medicine being at least one hemostatic agent including a beneficiated hectorite clay that is inert and non-reactive with blood for facilitating blood clotting.

40. The system according to claim 39, wherein the soluble release member dissolves at a hemorrhage site.

41. The system as recited in claim 39 wherein said hemostatic agent further comprises at least one additive.

42. The system as recited in claim 39 wherein said hemostatic agent further comprises a hydroxyethyl cellulose additive.

\* \* \* \* \*